United States Patent [19]

Sugawa et al.

[11] Patent Number: 6,150,567

[45] Date of Patent: Nov. 21, 2000

[54] PROCESS FOR THE REDUCTION OF CARBONYL COMPOUNDS

[75] Inventors: Tadashi Sugawa, Akashi; Tadashi Moroshima; Kenji Inoue, both of Kakogawa; Kazunori Kan, Nishinomiya, all of Japan

[73] Assignee: Kaneka Corporation, Osaka, Japan

[21] Appl. No.: 08/930,011

[22] PCT Filed: Jan. 29, 1997

[86] PCT No.: PCT/JP97/00189

§ 371 Date: Dec. 29, 1997

§ 102(e) Date: Dec. 29, 1997

[87] PCT Pub. No.: WO97/28105

PCT Pub. Date: Aug. 7, 1997

[30] Foreign Application Priority Data

Jan. 29, 1996 [JP] Japan .................................. 8-035632
Jan. 30, 1996 [JP] Japan .................................. 8-037256
Apr. 4, 1996 [JP] Japan .................................. 8-110317

[51] Int. Cl.[7] .................................................. C07C 27/04
[52] U.S. Cl. .......................... 568/814; 568/880; 568/881; 568/885; 564/502; 564/503
[58] Field of Search ..................... 568/309, 704, 568/705, 814, 861, 876, 878, 880, 881, 885; 564/502, 503, 186, 224

[56] References Cited

U.S. PATENT DOCUMENTS 5,523,463  6/1996  Hilpert ..................................... 560/137
5,591,885  1/1997  Hilpert ...................................... 560/29

FOREIGN PATENT DOCUMENTS 0 604 183 A1  6/1994  European Pat. Off. ...... C07D 215/48

63-297333  12/1988  Japan ............................. C07C 31/36

OTHER PUBLICATIONS

Heinsohn et al, Journal of Organic Chemistry, vol. 38, #25, pp. 4232–4236, 1973.

*Primary Examiner*—Sreeni Padmanabhan
*Attorney, Agent, or Firm*—Pollock, Vande Sande & Amernick

[57] ABSTRACT

The present invention provides a process for reducing carbonyl compounds to hydroxy compounds, in particular stereoselectively reducing α-aminohaloketone derivatives, under mild conditions in an easy and simple manner, which comprises reacting a carbonyl compound of the general formula (1) with an organoaluminum compound of the general formula (4) to provide the corresponding alcohol compound of the general formula (5).

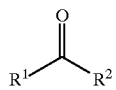

(1)

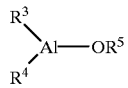

(4)

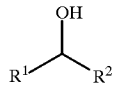

(5)

32 Claims, 10 Drawing Sheets

PROCESS FOR THE REDUCTION OF CARBONYL COMPOUNDS

This is the U.S. National Stage Application of PCT/JP97/00189 filed Jan. 29, 1997.

TECHNICAL FIELD

The present invention relates to a process for reducing carbonyl compounds.

BACKGROUND ART

Reduction of carbonyl compounds constitutes a very important technology in various fields, for example in the production of drug intermediates. As the so far known practical methods of reducing carbonyl compounds, there may be mentioned the Meerwein-Ponndorf-Varley reduction (MPV reduction) and the reduction using diisobutylaluminum hydride (DIBAH).

The MPV reduction is a method of reducing carbonyl compounds using an aluminum trialkoxide, such as Al(O-iPr)$_3$, as a reducing agent or reduction catalyst. This method is in frequent use as an economical method of reducing various ketones and aldehydes, since the aluminum trialkoxide used there and the alcohol such as isopropyl alcohol are inexpensive [Organic Reactions, volume 2, page 178 (1944)].

However, the MPV reduction, which uses an aluminum trialkoxide, has problems. The progress of the reaction tends to be very slow at low reaction temperatures mainly because of the low reactivity of said reagent. For increasing the reaction rate and the yield, a high reaction temperature not lower than 50° C., for example, is required. Said reduction is thus unsuited for the reduction of unstable carbonyl compounds or, in the case of carbonyl compounds showing low reactivity, the reduction reaction can hardly proceed even when the reaction temperature is raised.

The reduction of carbonyl compounds using DIBAH is a very useful method from the industrial viewpoint because of excellent reactivity and economics, among others. This method is in use, for example, for the reduction of α-aminochloroketone derivatives derived from leucine. When said α-aminochloroketone derivatives are reduced at −78° C. using DIBAH, the erythro form can be obtained preferentially with an about 75% diastereomer excess [Tetrahedron Letters, 36, 5453 (1995)].

The term "erythro form" as used herein means an isomer in which the neighboring amino and hydroxyl groups show the following relative configuration:

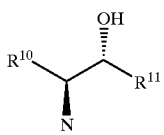

However, this reduction method requires a very low temperature in order that the reactivity may be controlled. Furthermore, when the method is applied to the reduction of said α-aminochloroketone derivatives, it is impossible to attain such a high stereoselectivity as 90% or more as expressed in terms of diastereomer excess.

Referring to the reduction reaction of carbonyl compounds with diisobutylaluminum hydride, the literature suggests the possibility that the diisobutylaluminum alkoxides formed as reaction intermediates be partly involved in the reduction reaction [Journal of Organic Chemistry, 38, 4232 (1973)]. However, no reports have ever suggested that dialkylaluminum monoalkoxides such as diisobutylaluminum isopropoxide might be effective in the reduction or stereoselective reduction of carbonyl compounds. Likewise, no reports have ever suggested that reducing agents prepared from a dialkylaluminum hydride, such as diisobutylaluminum hydride, and an alcohol, such as isopropyl alcohol, might be effective in the reduction or stereoselective reduction of carbonyl compounds.

In view of the foregoing, it is an object of the present invention to provide a method of reducing carbonyl compounds to the corresponding hydroxyl compounds in an easy and simple manner and under milder conditions. Another object is to provide a method of reducing certain carbonyl compounds that can hardly be reduced with ordinary aluminum trialkoxides and, in particular, a method for stereoselectively reducing α-aminoketone derivatives.

SUMMARY OF THE INVENTION

The gist of the present invention, which is directed to the reduction of carbonyl compounds, consists in that a carbonyl compound of the general formula (1)

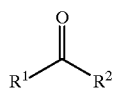

(1)

(wherein R$^1$ and R$^2$ each independently represents a substituted or unsubstituted alkyl group containing 1 to 30 carbon atoms, a substituted or unsubstituted aralkyl group containing 7 to 30 carbon atoms, a substituted or unsubstituted aryl group containing 6 to 30 carbon atoms, a cyano group, a hydrogen atom, a group of the general formula (2)

$$CH_nX_{3-n} \qquad (2)$$

(in which X represents a halogen atom and n represents an integer of 0 to 2), or a group of the general formula (3)

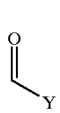

(3)

(in which Y represents an alkoxyl group, an aralkyloxyl group, a substituted or unsubstituted amino group or an alkylthio group), provided that one of R$^1$ and R$^2$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms) is reacted with an organoaluminum compound of the general formula (4)

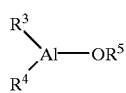

(4)

(wherein R$^3$ and R$^4$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms and $R^5$ represents a substituted or unsubstituted primary alkyl group containing 1 to 20 carbon atoms, a substituted or unsubstituted secondary alkyl group containing 1 to 20 carbon atoms, a substituted or unsubstituted primary aralkyl group containing 7 to 30 carbon atoms or a substituted or unsubstituted secondary aralkyl group containing 7 to 30 carbon atoms) to provide the corresponding alcohol compound of the general formula (5)

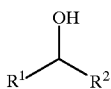

(5)

(wherein $R^1$ and $R^2$ are as defined above).

DETAILED DESCRIPTION OF THE INVENTION

Figure 1:
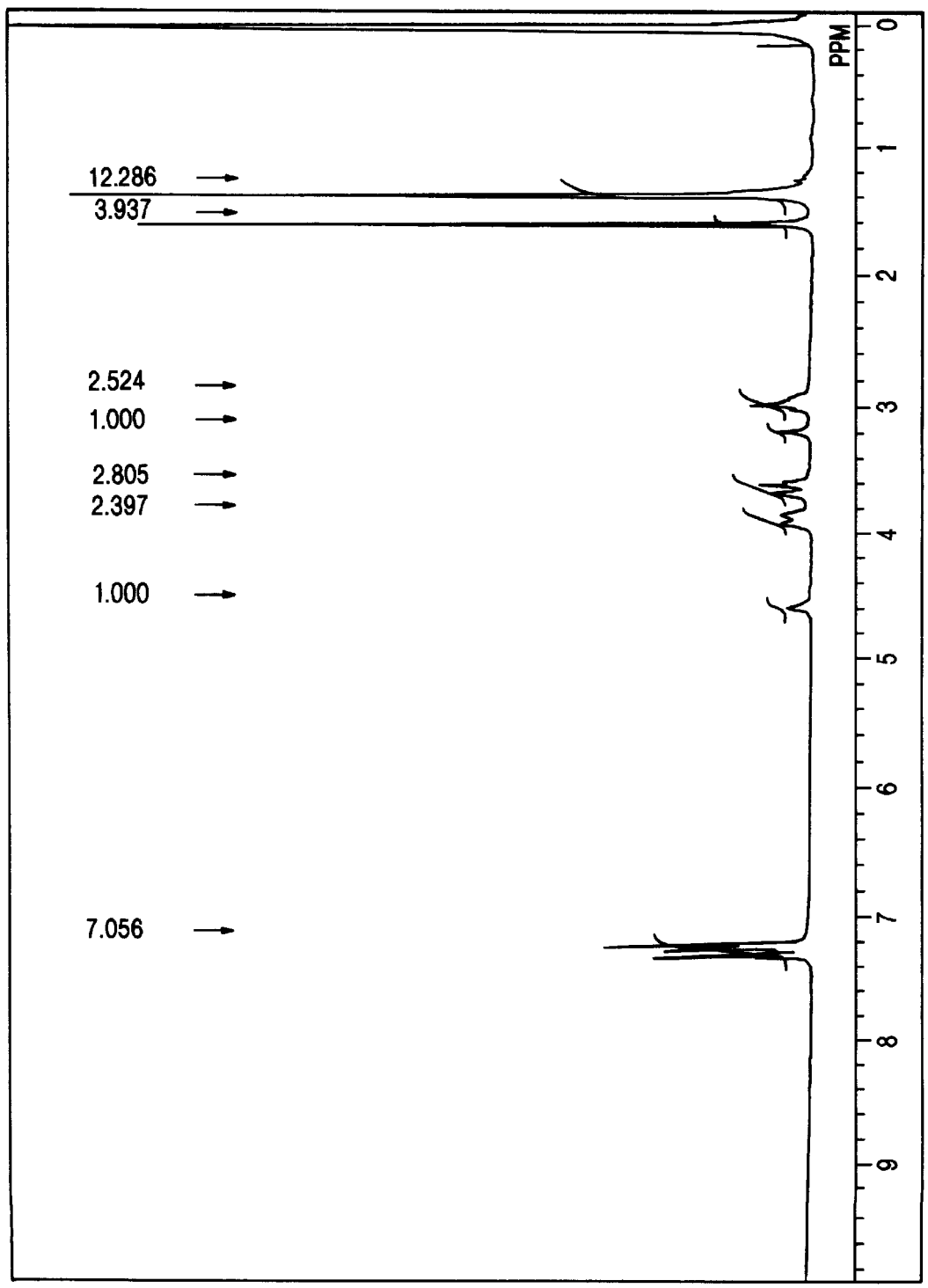
FIG. 1 shows an NMR sepctrum of the product obtained in Example 5, namely t-butyl [1(S)-benzyl-2(S)-hydroxy-3-chloropropyl]carbamate.

Referring to the carbonyl compounds of the above general formula (1), $R^1$ and $R^2$ each independently represents a substituted or unsubstituted alkyl group containing 1 to 30 carbon atoms, a substituted or unsubstituted aralkyl group containing 7 to 30 carbon atoms, a substituted or unsubstituted aryl group containing 6 to 30 carbon atoms, a cyano group, a hydrogen atom, a group of the above general formula (2) or a group of the above general formula (3), provided that one of $R^1$ and $R^2$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms.

As the substituent, there may be mentioned a halogen atom, an alkoxycarbonyl group, an alkoxyl group, a protected amino group, a cyano group, a nitro group, a sulfinyl group, a sulfonyl group, an alkylthio group and the like. Each group represented by $R^1$ or $R^2$ may have two or more such substituents.

The above-mentioned substituted or unsubstituted alkyl group containing 1 to 30 carbon atoms is not limited to any particular species but includes, for example, methyl, ethyl, butyl, isopropyl, cyclohexyl and the like. Preferred are those groups which contain 1 to 20 carbon atoms.

The above-mentioned substituted or unsubstituted aralkyl group containing 7 to 30 carbon atoms is not limited to any particular species but includes, for example, benzyl, phenylpropyl, phenylethyl, p-methoxybenzyl, 1-(N-t-butoxycarbonylamino)-2-phenylethyl, 1-(N-benzyloxycarbonylamino)-2-phenylethyl and the like. Preferred are those groups which contain 7 to 20 carbon atoms.

The above-mentioned substituted or unsubstituted aryl group containing 6 to 30 carbon atoms is not limited to any particular species but includes, for example, phenyl, p-chlorophenyl, p-nitrophenyl, naphthyl and the like. Preferred are those groups which contain 6 to 20 carbon atoms.

Referring to the group represented by the above general formula (2), X represents a halogen atom and n represents an integer of 0 to 2.

Said halogen atom is not limited to any particular species but includes a chlorine atom, a bromine atom, an iodine atom or a fluorine atom and preferably is a chlorine atom.

The above-mentioned group of general formula (2) is not limited to any particular species but includes, among others, chloromethyl, dichloromethyl, trichloromethyl, bromomethyl, dibromomethyl, tribromomethyl, fluoromethyl, difluoromethyl, trifluoromethyl, iodomethyl, diiodomethyl, triiodomethyl and the like. Preferred among them are chloromethyl, dichloromethyl and trichloromethyl.

Referring to the above-mentioned group of general formula (3), Y represents an alkoxyl group, an aralkyloxyl group, a substituted or unsubstituted amino group or an alkylthio group.

Said alkoxyl group is not limited to any particular species but includes, for example, methoxy, ethoxy, t-butoxy and the like. Preferred are those containing 1 to 10 carbon atoms.

The above-mentioned aralkyloxyl group is not limited to any particular species but includes benzyloxyl and the like, among others. Preferred are those groups which contain 6 to 20 carbon atoms.

The above-mentioned substituted or unsubstituted amino group is not limited to any particular species but includes, for example, amino, dimethylamino and the like.

The above-mentioned alkylthio group is not limited to any particular species but includes methylthio, phenylthio and the like, among others.

The above-mentioned group of general formula (3) is not limited to any particular species but includes, among others, methoxycarbonyl, ethoxycarbonyl, benzyloxycarbonyl, t-butoxycarbonyl and the like. Preferred are methoxycarbonyl and ethoxycarbonyl, however.

As the above-mentioned carbonyl compound of general formula (1), there may be mentioned, for example, aldehydes such as benzaldehyde, isobutylaldehyde, etc.; and ketones such as acetophenone, propiophenone, cyclohexanone, ethyl acetoacetate, methyl benzoylformate, phenacyl chloride, α-dichloroacetophenone, α-trichloroacetophenone, ethyl 4-chloroacetoacetate, benzoyl cyanide, t-butyl 1(S)-benzyl-2-oxo-3,3-dichloropropylcarbamate, t-butyl 1(S)-benzyl-2-oxo-3,3,3-trichloropropylcarbamate, methyl 3(S)-(N-benzyloxycarbonylamino)-2-oxo-4-phenylacetate, etc.

Referring to the above-defined symbols $R^3$ and $R^4$, the substituted or unsubstituted alkyl group containing 1 to 10 carbon atoms is not limited to any particular species but includes, for example, methyl, ethyl, n-butyl, isobutyl, isopropyl, cyclohexyl, methoxymethyl and the like. Said group preferably contains 1 to 6 carbon atoms and is more preferably isobutyl.

Further referring to the symbols $R^3$ and $R^4$, the aralkyl group containing 7 to 20 carbon atoms is not limited to any particular species but includes, for example, benzyl, 3-phenyl-1-propyl, α-phenylethyl, p-methoxybenzyl and the like. Those containing 7 to 15 carbon atoms are preferred.

Again referring to the symbols $R^3$ and $R^4$, the aryl group containing 6 to 20 carbon atoms is not limited to any particular species but includes, for example, phenyl, p-hydroxyphenyl, p-chlorophenyl, p-nitrophenyl, naphthyl and the like. Those containing 6 to 15 carbon atoms are preferred.

Referring to the symbol $R^5$ defined above, the substituted or unsubstituted primary alkyl group containing 1 to 20 carbon atoms or the substituted or unsubstituted secondary alkyl group containing 1 to 20 carbon atoms is, for example, methyl, ethyl, isopropyl, cyclohexyl, 2,4-dimethyl-3-pentyl or the like. Preferred are those containing 1 to 10 carbon atoms. More preferred are isopropyl, cyclohexyl and 2,4-dimethyl-3-pentyl.

Referring to the symbol $R^5$, the substituted or unsubstituted primary aralkyl group containing 7 to 30 carbon atoms or the substituted or unsubstituted secondary aralkyl group containing 7 to 30 carbon atoms is, for example, benzhydryl, benzyl, phenylpropyl, α-phenylethyl, p-methoxybenzyl and the like. Those containing 7 to 15 carbon atoms are preferred and benzhydryl is more preferred.

As the organoaluminum compound represented by the above general formula (4), there may be mentioned, among others, diisobutylaluminum isopropoxide, diisobutylaluminum diphenylmethoxide, diisobutylaluminum ethoxide, diisobutylaluminum cyclohexyloxide, diisobutylaluminum 2,4-dimethyl-3-pentyloxide, diethylaluminum ethoxide and the like. Among them, diisobutylaluminum isopropoxide and diisobutylaluminum diphenylmethoxide are preferred.

The organoaluminum compound of the above general formula (4) can be prepared, for example, by (1) the reaction of a dialkylaluminum hydride with an alcohol, (2) the reaction of a trialkylaluminum with an alcohol (German Patent Specification No. 2507532), (3) the use, as such, of the reaction mixture obtained upon reduction of a carbonyl compound, such as acetone, with DIBAH, (4) the reaction of a trialkylaluminum with a trialkoxyaluminum (German Patent Specification No. 2304617), or (5) the reaction of a trialkylaluminum with a trialkyl borate (German Patent Specification No. 2151176).

The process for reducing carbonyl compounds according to the present invention can be applied to the reduction of α-aminoketone derivatives of the general formula (6) shown below and the reduction of α-aminohaloketone derivatives of the general formula (7) shown below. The process for reducing carbonyl compounds according to the present invention makes it possible to produce α-aminoalcohol derivatives of the general formula (8) shown below from the α-aminoketone derivatives of general formula (6) or produce α-aminohalohydrin derivatives of the general formula (9) shown below from the α-aminohaloketone derivatives of general formula (7). These α-aminoalcohol derivatives and α-aminohalohydrin derivatives are compounds useful as intermediates for medicinal compounds.

The process for producing the α-aminoalcohol derivatives mentioned above comprises reacting an α-aminoketone derivative of the general formula (6)

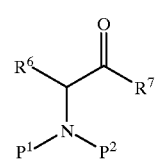

(6)

(wherein $R^6$ represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms or a hydrogen atom, $R^7$ represents a group of the above general formula (2) or a group of the above general formula (3) and $P^1$ and $P^2$ each independently represents a hydrogen atom or an amino-protecting group or $P^1$ in combination with $P^2$ represent a phthaloyl group, with the exception of the case in which $P^1$ and $P^2$ are the same and each is a hydrogen atom), in particular an α-aminohaloketone derivative of the general formula (7)

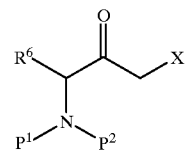

(7)

(wherein X represents a halogen atom and $R^6$ is as defined above) with an organoaluminum compound of the above general formula (4) to provide the corresponding α-aminoalcohol derivative of the general formula (8)

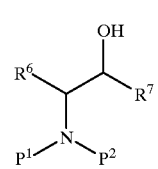

(8)

(wherein $R^6$, $R^7$, $P^1$ and $P^2$ are as defined above), in particular the corresponding α-aminohalohydrin derivative of the general formula (9)

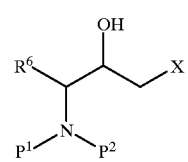

(9)

(wherein X, $R^6$, $P^1$ and $P^2$ are as defined above).

Referring to the above-mentioned α-aminoketone derivative of general formula (6) and α-aminohaloketone derivative of general formula (7), $R^6$ is the side chain of a familiar α-amino acid or the side chain of an α-amino acid derivative obtained by processing such a familiar α-amino acid and represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms or a hydrogen atom.

Said substituted or unsubstituted alkyl group containing 1 to 20 carbon atoms is not limited to any particular species but includes, for example, methyl, ethyl, isopropyl, isobutyl, t-butyl, hydroxymethyl, 1-hydroxyethyl, mercaptomethyl, methylthiomethyl, etc. Preferred are those containing 1 to 10 carbon atoms.

Said substituted or unsubstituted aralkyl group containing 7 to 20 carbon atoms is not limited to any particular species but includes, for example, benzyl, p-hydroxybenzyl, p-methoxybenzyl, phenylthiomethyl, α-phenethyl, etc. Preferred are those containing 7 to 15 carbon atoms.

Said substituted or unsubstituted aryl group containing 6 to 20 carbon atoms is not limited to any particular species but includes, for example, phenyl, p-hydroxyphenyl, p-methoxyphenyl, etc. Preferred are those containing 6 to 15 carbon atoms.

Referring to the above-mentioned α-aminoketone derivatives of general formula (6) and to the above-mentioned α-aminohaloketone derivatives of general formula (7), $P^1$ and $P^2$ each independently represents a hydrogen atom or an amino-protecting group or $P^1$ in combination with $P^2$ represent a phthaloyl group, with the exception of the case in which $P^1$ and $P^2$ are the same and each is a hydrogen atom.

Said amino-protecting group is not limited to any particular species provided that it is effective in protecting the amino group from the reduction reaction in question. It thus includes such protective groups as those described in Theodora W. Green: Protective Groups in Organic Synthesis, 2nd edition, John Wiley & Sons, 1990, pp. 309 to 384, for example, ethoxycarbonyl, methoxycarbonyl, t-butoxycarbonyl, benzyloxycarbonyl, acetyl, trifluoroacetyl, benzyl, dibenzyl, tosyl, benzoyl, phthaloyl, etc. The amino-protecting group should preferably be selected taking the stereoselectivity of the reduction reaction into consideration. The reduction reaction can be caused to proceed with high erythroselectivity by employing, for example, such an alkoxycarbonyl group as methoxycarbonyl, t-butoxycarbonyl or ethoxycarbonyl or such an aralkyloxy carbonyl group as benzyloxycarbonyl.

Referring to the above-mentioned α-aminoketone derivatives of general formula (6), $R^7$ represents a group of the above general formula (2) or a group of the above general formula (3).

Referring to the above-mentioned α-aminohaloketone derivatives of general formula (7), X represents a halogen atom.

Said halogen atom is not limited to any particular species but may be a chlorine, bromine, iodine or fluorine atom. It is preferably a chlorine atom, however.

The above-mentioned α-aminoketone derivatives of general formula (6) includes, but is not limited to, optically active t-butyl (S)-(1-benzyl-3-chloro-2-oxopropyl) carbamate, t-butyl (R)-(1-benzyl-3-chloro-2-oxopropyl) carbamate, methyl (S)-(1-benzyl-3-chloro-2-oxopropyl) carbamate, methyl (R)-(1-benzyl-3-chloro-2-oxopropyl) carbamate, ethyl (S)-(1-benzyl-3-chloro-2-oxopropyl) carbamate, ethyl (R)-(1-benzyl-3-chloro-2-oxopropyl) carbamate, benzyl (S)-(1-phenylthiomethyl-3-chloro-2-oxopropyl)carbamate, benzyl (R)-(1-phenylthiomethyl-3-chloro-2-oxopropyl)carbamate, t-butyl (S)-(1-phenylthiomethyl-3-chloro-2-oxopropyl)carbamate, t-butyl (R)-(1-phenylthiomethyl-3-chloro-2-oxopropyl)carbamate, methyl (S)-(1-phenylthiomethyl-3-chloro-2-oxopropyl) carbamate, methyl (R)-(1-phenylthiomethyl-3-chloro-2-oxopropyl)carbamate, methyl (S)-(t-butoxycarbonylamino)-2-oxo-4-phenylbutyrate, methyl (R)-(t-butoxycarbonylamino)-2-oxo-4-phenylbutyrate, methyl (S)-(methoxycarbonylamino)-2-oxo-4-phenylbutyrate, methyl (R)-(methoxycarbonylamino)-2-oxo-4-phenylbutyrate, benzyl [1(S)-benzyl-2-oxo-3,3,3-trichloropropyl]carbamate, benzyl [1(R)-benzyl-2-oxo-3,3,3-trichloropropyl] carbamate, ethyl [1(S)-benzyl-3,3-dichloro-2-oxopropyl] carbamate, ethyl [1(R)-benzyl-3,3-dichloro-2-oxopropyl] carbamate, etc.

The above-mentioned α-aminohaloketone derivatives includes, but is not limited to, optically active t-butyl (S)-(1-benzyl-3-chloro-2-oxopropyl)carbamate, t-butyl (R)-(1-benzyl-3-chloro-2-oxopropyl)carbamate, methyl (S)-(1-benzyl-3-chloro-2-oxopropyl)carbamate, methyl (R)-(1-benzyl-3-chloro-2-oxopropyl)carbamate, ethyl (S)-(1-benzyl-3-chloro-2-oxopropyl)carbamate, ethyl (R)-(1-benzyl-3-chloro-2-oxopropyl)carbamate, benzyl (S)-(1-benzyl-3-chloro-2-oxopropyl)carbamate, benzyl (R)-(1-benzyl-3-chloro-2-oxopropyl)carbamate, benzyl (S)-(1-phenylthiomethyl-3-chloro-2-oxopropyl)carbamate, benzyl (R)-(1-phenylthiomethyl-3-chloro-2-oxopropyl)carbamate, t-butyl (S)-(1-phenylthiomethyl-3-chloro-2-oxopropyl) carbamate, t-butyl (R)-(1-phenylthiomethyl-3-chloro-2-oxopropyl)carbamate, methyl (S)-(1-phenylthiomethyl-3-chloro-2-oxopropyl)carbamate, methyl (R)-(1-phenylthiomethyl-3-chloro-2-oxopropyl)carbamate, ethyl (S)-(1-phenylthiomethyl-3-chloro-2-oxopropyl)carbamate, ethyl (R)-(1-phenylthiomethyl-3-chloro-2-oxopropyl) carbamate, etc. Preferred among these are t-butyl (S)-(1-benzyl-3-chloro-2-oxopropyl)carbamate and benzyl (S)-(1-phenylthiomethyl-3-chloro-2-oxopropyl)carbamate.

Referring now to the process for reducing carbonyl compounds according to the present invention, the reduction of the carbonyl compound of general formula (1) is effected by adding the carbonyl compound of general formula (1) to the reaction system or adding the reducing agent to the carbonyl compound of general formula (1), followed by stirring. The reduction reaction is preferably carried out at a temperature of −10 to 60° C., more preferably −10 to 30° C.

The organoaluminum compound of general formula (4) is added preferably in an amount of 1 to 5 molar equivalents, more preferably 1.5 to 3 molar equivalents, relative to the carbonyl compound of general formula (1).

The solvent to be used in the practice of the present invention is not limited to any particular species but includes, among others, alcohol compounds of the formula $R^5OH$ in which $R^5$ is the same as $R^5$ in the general formula (4) shown above, as well as toluene, hexane, cyclohexane, heptane, tetrahydrofuran, t-butyl methyl ether, 1,2-dimethoxyethane, methylene chloride, N,N-dimethylformamide and the like. Preferred among the solvents other than the alcohols mentioned above are toluene, tetrahydrofuran and hexane.

Although the procedure for after-treatment is not limited to any particular one, the product alcohol compound of general formula (5) can be recovered after completion of the reaction by an ordinary after-treatment and isolation procedure, for example, by hydrolyzing the reaction mixture with an aqueous acid solution, extracting the same, concentrating the extract and then subjecting the concentrate to isolation treatment using a column, crystallization, distillation and/or the like.

The compound of the above-mentioned general formula (4) can also be prepared by the reaction mentioned below and the thus-prepared reaction mixture can be used as such for the reduction of carbonyl compounds of general formula (1), (6) or (7).

Thus, the preparation product obtained by reacting an organoaluminum compound of the general formula (10)

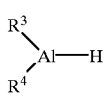

(10)

(wherein $R^3$ and $R^4$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms) with an alcohol compound of the general formula (11)

$$R^5—OH \qquad (11)$$

(wherein $R^5$ is a substituted or unsubstituted primary alkyl group containing 1 to 20 carbon atoms, a substituted or unsubstituted secondary alkyl group containing 1 to 20 carbon atoms, a substituted or unsubstituted primary aralkyl group containing 7 to 30 carbon atoms or a substituted or unsubstituted secondary aralkyl group containing 7 to 30 carbon atoms) can be used for the reduction of the carbonyl compounds mentioned above.

The organoaluminum compound of the above general formula (10) is, for example, diethylaluminum hydride, diisobutylaluminum hydride and the like. Preferred among them is diisobutylaluminum hydride.

The alcohol compound of the above general formula (11) is not limited to any particular species provided that it is high in hydrogen ion-donating ability. As examples, there may be mentioned isopropanol, benzhydrol, 2,4-dimethyl-3-pentanol, cyclohexanol, 2-methoxycyclohexanol and the like. Preferred are alcohol compounds of the general formula (12)

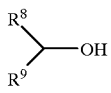

(12)

(wherein $R^8$ and $R^9$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms or $R^8$ in combination with $R^9$ represent a cycloalkyl group). More preferred are isopropanol and benzhydrol.

Said substituted or unsubstituted alkyl group containing 1 to 10 carbon atoms is, for example, methyl, ethyl, isopropyl or the like. Methyl is preferred, however.

Said substituted or unsubstituted aralkyl group containing 7 to 20 carbon atoms is, for example, benzyl, phenylpropyl, α-phenylethyl, p-methoxybenzyl or the like.

Said substituted or unsubstituted aryl group containing 6 to 20 carbon atoms is, for example, phenyl, p-hydroxyphenyl, p-chlorophenyl, p-nitrophenyl, naphthyl or the like.

Said cycloalkyl group is, for example, cyclohexyl, cyclopentyl or the like.

The process for reducing carbonyl compounds according to the present invention can be carried out, for example, in the following manner.

First, the reducing agent is prepared by reacting the organoaluminum compound of general formula (10) with the alcohol compound of general formula (11).

Said organoaluminum compound of general formula (10) is used in an amount below 3 molar equivalents, preferably in an amount of 1 to 5 molar equivalents, more preferably 1.5 to 3 molar equivalents, relative to the carbonyl compound of general formula (1).

Said alcohol of general formula (11) is added in an amount below 3 molar equivalents, preferably in an amount of 1 to 2 molar equivalents, relative to the organoaluminum compound of general formula (10).

The preparation of the reducing agent by reacting said organoaluminum compound of general formula (10) with said alcohol compound of general formula (11) can be carried out, for example, by adding the alcohol compound of general formula (11) to a solution of the organoaluminum compound of general formula (10) in toluene, tetrahydrofuran, hexane or the like and then stirring the mixture. The addition conditions are not critical but the addition is preferably carried out at −10 to 60° C., more preferably 0 to 40° C. The stirring conditions are not critical but the sitrring is preferably carried out at 0 to 30° C. for 1 to 10 hours. It is also possible to add the organoaluminum compound of general formula (10) to the alcohol compound of general formula (11).

Then, the carbonyl compound of general formula (1) is added to the reaction system, or the reducing agent is added to the carbonyl compound of general formula (1), and the mixture is stirred to effect the reduction of the carbonyl compound of general formula (1). The reduction temperature is preferably within the range of −10 to 60° C., more preferably −10 to 30° C.

In accordance with the present invention, the carbonyl compound is reduced using an alkylaluminum alkoxide differing from the one derivable from the reactant carbonyl compound. In this case, by adequately selecting the alkoxide group of said alkylaluminum alkoxide in view of the alkoxide group formed as an intermediate from the carbonyl compound, it becomes possible to increase the rate of intermediate formation, carry out the reaction at low temperatures and control the configuration of the reduction product alcohol. It is possible to reduce the carbonyl compound of formula (1), (6) or (7) under mild conditions and, furthermore, it is possible to stereoselectively reduce certain carbonyl compounds, for example α-keto ester derivatives, which can hardly be reduced with ordinary aluminum trialkoxides.

By adequately selecting the above-mentioned aminoprotecting group, for example, it is possible to produce the erythro form of the α-aminoalcohol derivative of general formula (8) or of the α-aminohalohydrin derivative of general formula (9) with very high stereoselectivity. Thus, for example, in the case of reduction of optically active t-butyl (S)-(1-benzyl-3-chloro-2-oxopropyl)carbamate, which is a phenylalanine derivative, the corresponding optically active aminohalohydrin can be obtained with a diastereomer excess (d.e.) of not lower than 94%. When benzhydrol, for instance, is used as the alcohol compound, the corresponding optically active aminohalohydrin can be obtained with a surprisingly high diastereomer excess of 98%. In the case of reduction of methyl (S)-(t-butoxy carbonylamino)-2-oxo-4-phenylbutyrate, too, the corresponding optically active α-hydroxyester can be obtained with a high erythroselectivity. The starting α-aminoketone derivative of general formula (7) can generally be produced by reacting the corresponding α-amino acid derivative (e.g. α-amino acid ester) with the magnesium enolate of α-chloroacetic acid, for instance (Japanese Patent Application Hei-07-273547). An HIV protease inhibitor can readily be derived from the optically active aminohalohydrin mentioned above (Japanese Kokai Publication Hei-08-99959).

BEST MODE FOR CARRYING OUT THE INVENTION

The following examples are further illustrative of the present invention but are by no means limitative of the scope of the present invention.

EXAMPLE 1

Production of t-butyl [1(S)-benzyl-2(S)-hydroxy-3-chloropropyl]carbamate (I)

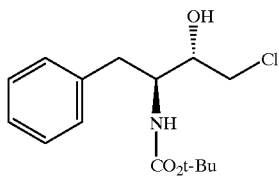

(I)

To an ice-cooled 1.0 M solution of triisobutylaluminum in hexane (10.5 ml, 10.5 mmol) was added 0.76 ml (10 mmol) of 2-propanol, and the mixture was stirred at room temperature for 30 minutes. After dilution of the mixture with 10 ml of toluene, 0.759 g (2.5 mmol) of t-butyl [1(S)-benzyl-2-oxo-3-chloropropyl]carbamate was added and the resultant mixture was stirred at room temperature for 2 hours. Hydrolysis with 1 N hydrochloric acid, extraction with ethyl acetate and concentration gave 0.840 g of pale-yellow crystals. The crystals obtained were subjected to quantitative analysis by HPLC and the yield and selectivity were determined.

Yields: t-butyl [1(S)-benzyl-2(S)-hydroxy-3-chloropropyl]carbamate 97.4%; t-butyl [1(S)-benzyl-2(R)-hydroxy-3-chloropropyl]carbamate 2.6%. Selectivity: (1S, 2S) form/(1S,2R) form=97.4/2.6.

EXAMPLE 2

Production of t-butyl [1(S)-benzyl-2(S)-hydroxy-3-chloropropyl]carbamate (I)

To a 1.0 M solution of triisobutylaluminum in hexane (10.5 ml, 10.5 mmol) was added 0.47 g (2.5 mmol) of triisopropoxyborane, and the mixture was heated at 170° C. for 2 hours. After cooling to 80° C., the pressure was reduced to 10 mmHg to thereby cause the excess triisobutylborane to distill off. After cooling to room temperature and dilution with 20 ml of toluene, 0.744 g (2.5 mmol) of t-butyl [1(S)-benzyl-2-oxo-3-chloropropyl]carbamate was added and the resultant mixture was stirred at room temperature for 3 hours. Hydrolysis with 1 N hydrochloric acid, extraction with ethyl acetate and concentration gave 0.995 g of pale-yellow crystals. The crystals obtained were subjected to quantitative analysis by HPLC and the yield and selectivity were determined.

Yields: t-butyl [1(S)-benzyl-2(S)-hydroxy-3-chloropropyl]carbamate 80.1%; t-butyl [1(S)-benzyl-2(R)-hydroxy-3-chloropropyl]carbamate 3.4%. Selectivity: (1S, 2S) form/(1S,2R) form=95.9/4.1.

EXAMPLE 3

Production of t-butyl [1(S)-benzyl-2(S)-hydroxy-3-chloropropyl]carbamate (I)

A hexane solution of diethylaluminum ethoxide (about 1 M, 10.4 ml, 10.4 mmol) was diluted with 18 ml of toluene, then 1.489 g (5 mmol) of t-butyl [1(S)-benzyl-2-keto-3-chloropropyl]carbamate was added, and the mixture was stirred at room temperature for 24 hours. After quenching with 1 N hydrochloric acid, the mixture was extracted with ethyl acetate. Concentration of the extract gave 2.560 g of pale-yellow crystals. The crystals obtained were subjected to quantitative analysis by HPLC and the yield and selectivity were determined.

Yields: t-butyl [1(S)-benzyl-2(S)-hydroxy-3-chloropropyl]carbamate 55.7%; t-butyl [1(S)-benzyl-2(R)-hydroxy-3-chloropropyl]carbamate 8.3%. Selectivity: (1S, 2S) form/(1S,2R) form=87/13.

EXAMPLE 4

Production of t-butyl [1(S)-benzyl-2(S)-hydroxy-3-chloropropyl]carbamate (I)

Acetone (581 mg, 10 mmol) was added to 9.9 ml (10 mmol) of a toluene solution of DIBAH (1.02 M) at room temperature and the mixture was stirred at room temperature for 1 hour. Then, 1.489 g (5 mmol) of t-butyl [1(S)-benzyl-2-oxo-3-chloropropyl]carbamate was added and the resultant mixture was stirred at room temperature for 2 hours. After hydrolysis with 1 N hydrochloric acid, the reaction mixture was extracted with ethyl acetate. Concentration of the extract gave 1.635 g of pale-yellow crystals. The crystals obtained were subjected to quantitative analysis by HPLC and the yield and selectivity were determined.

Yields: t-butyl [1(S)-benzyl-2(S)-hydroxy-3-chloropropyl]carbamate 82.6%; t-butyl [1(S)-benzyl-2(R)-hydroxy-3-chloropropyl]carbamate 4.1%. Selectivity: (1S, 2S) form/(1S,2R) form=95.2/4.8.

EXAMPLE 5

Production of t-butyl [1(S)-benzyl-2(S)-hydroxy-3-chloropropyl]carbamate (I)

2-Propanol (1.53 ml, 20 mmol) was added to 9.8 ml (10 mmol) of a toluene solution of DIBAH (1.02 M) at room temperature and the mixture was stirred at room temperature for 1 hour. Thereto was added 1.489 g (5.0 mmol) of t-butyl [1(S)-benzyl-2-oxo-3-chloropropyl]carbamate, and the resultant mixture was stirred at room temperature for 2 hours, followed by hydrolysis with 1 N hydrochloric acid under cooling with ice. Extraction with ethyl acetate and concentration gave 1.61 g of pale-yellow crystals. Purification by silicagel column chromatography (hexane/ethyl acetate) gave 1.386 g of t-butyl [1(S)-benzyl-2(S)-hydroxy-3-chloropropyl]carbamate (yield: 92.5%) and 33 mg of t-butyl [1(S)-benzyl-2(R)-hydroxy-3-chloropropyl] carbamate (yield: 2.2%). [(1S,2S) form/(1S,2S) form=97.7/2.3].

Figure 2:
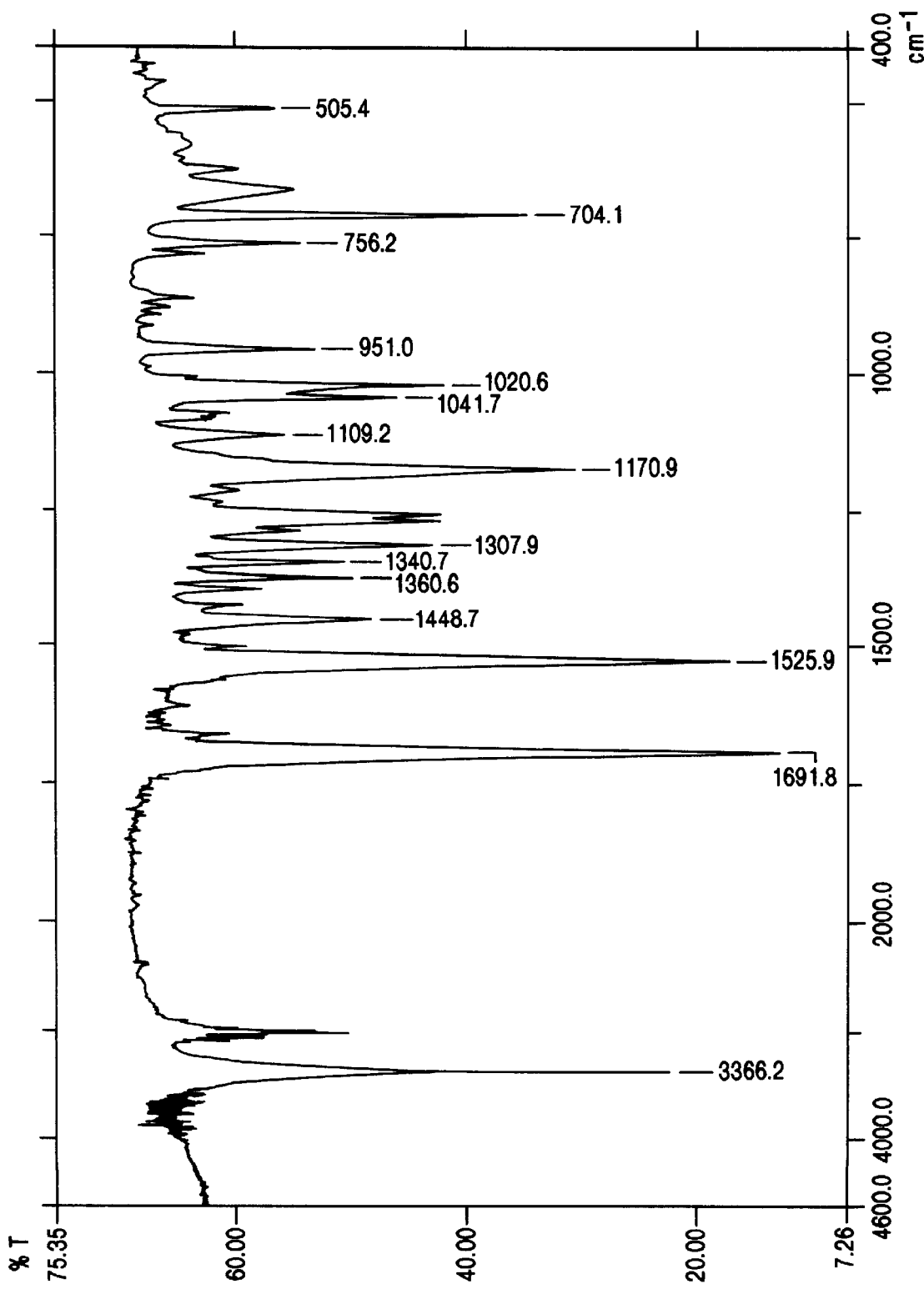
FIG. 2 shows an IR spectrum of the product obtained in Example 5, namely t-butyl [1(S)-benzyl-2(S)-hydroxy-3-chloropropyl]carbamate.

An NMR spectrum of the thus-obtained product t-butyl [1(S)-benzyl-2(S)-hydroxy-3-chloropropyl]carbamate is shown in FIG. 1 and an IR spectrum of the same in FIG. 2.

$[\alpha_D^{25}]=-3.44$ (c=1.05, MeOH)

Melting point: 168.5 to 169.5° C.

EXAMPLE 6

Production of t-butyl [1(S)-benzyl-2(S)-hydroxy-3-chloropropyl]carbamate (I)

Benzhydrol (3.68 g, 20 mmol) was added to 9.9 ml (10 mmol) of a toluene solution of DIBAH (1.02 M) at room temperature, followed by addition of 20 ml of toluene. After stirring the mixture at room temperature for 1 hour, 1.489 g (5 mmol) of t-butyl [1(S)-benzyl-2-oxo-3-chloropropyl] carbamate was added and the resultant mixture was stirred at room temperature for 2 hours. After hydrolysis with 1 N hydrochloric acid, the reaction mixture was extracted with ethyl acetate and the organic layer obtained was subjected to quantitative analysis by HPLC and the yield and selectivity were determined.

Yields: t-butyl [1(S)-benzyl-2(S)-hydroxy-3-chloropropyl]carbamate 99.1%; t-butyl [1(S)-benzyl-2(R)-hydroxy-3-chloropropyl]carbamate 0.9%.

Selectivity: (1S,2S) form/(1S,2R) form=99.1/0.9.

EXAMPLE 7

Production of t-butyl [1(S)-benzyl-2(S)-hydroxy-3-chloropropyl]carbamate (I)

Cyclohexanol (2.0 g, 20 mmol) and 10 ml of toluene were added to 9.8 ml (10 mmol) of a toluene solution of DIBAH (1.02 M) at room temperature and the mixture was stirred at room temperature for 1 hour. Thereto was added 1.489 g (5.0 mmol) of t-butyl [1(S)-benzyl-2-oxo-3-chloropropyl] carbamate, and the resultant mixture was stirred at room temperature for 2 hours, followed by hydrolysis with 1 N hydrochloric acid with ice cooling. Extraction with ethyl acetate and concentration gave 1.53 g of pale-yellow crystals. The crystals obtained were subjected to quantitative analysis by HPLC and the yield and selectivity were determined.

Yields: t-butyl [1(S)-benzyl-2(S)-hydroxy-3-chloropropyl]carbamate 93.4%; t-butyl [1(S)-benzyl-2(R)-hydroxy-3-chloropropyl]carbamate 2.9%.

Selectivity: (1S,2S) form/(1S,2R) form=97.0/3.0.

EXAMPLE 8

Production of methyl [1(S)-benzyl-2(S)-hydroxy-3-chloropropyl]carbamate (II)

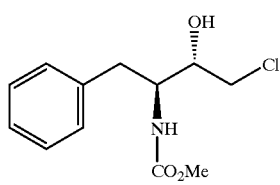

(II)

The procedure of Example 1 was followed using 1.28 g (5 mmol) of methyl [1(S)-benzyl-2-oxo-3-chloropropyl] carbamate in lieu of t-butyl [1(S)-benzyl-2-oxo-3-chloropropyl]carbamate, to give 1.314 g of pale-yellow crystals. Recrystallization from hexane/ethyl acetate/ethanol gave 1.063 g of methyl [1(S)-benzyl-2(S)-hydroxy-3-chloropropyl]carbamate (yield: 78.0%). Analysis of the mother liquor by HPLC revealed the presence of 60.0 mg of methyl [1(S)-benzyl-2(S)-hydroxy-3-chloropropyl] carbamate (yield: 4.5%) and 36.1 mg of methyl [1(S)-benzyl-2(R)-hydroxy-3-chloropropyl]carbamate (yield: 2.8%). Selectivity with respect to the total reaction products: (1S,2S) form/(1S,2R) form=96.7/3.3.

Figure 3:
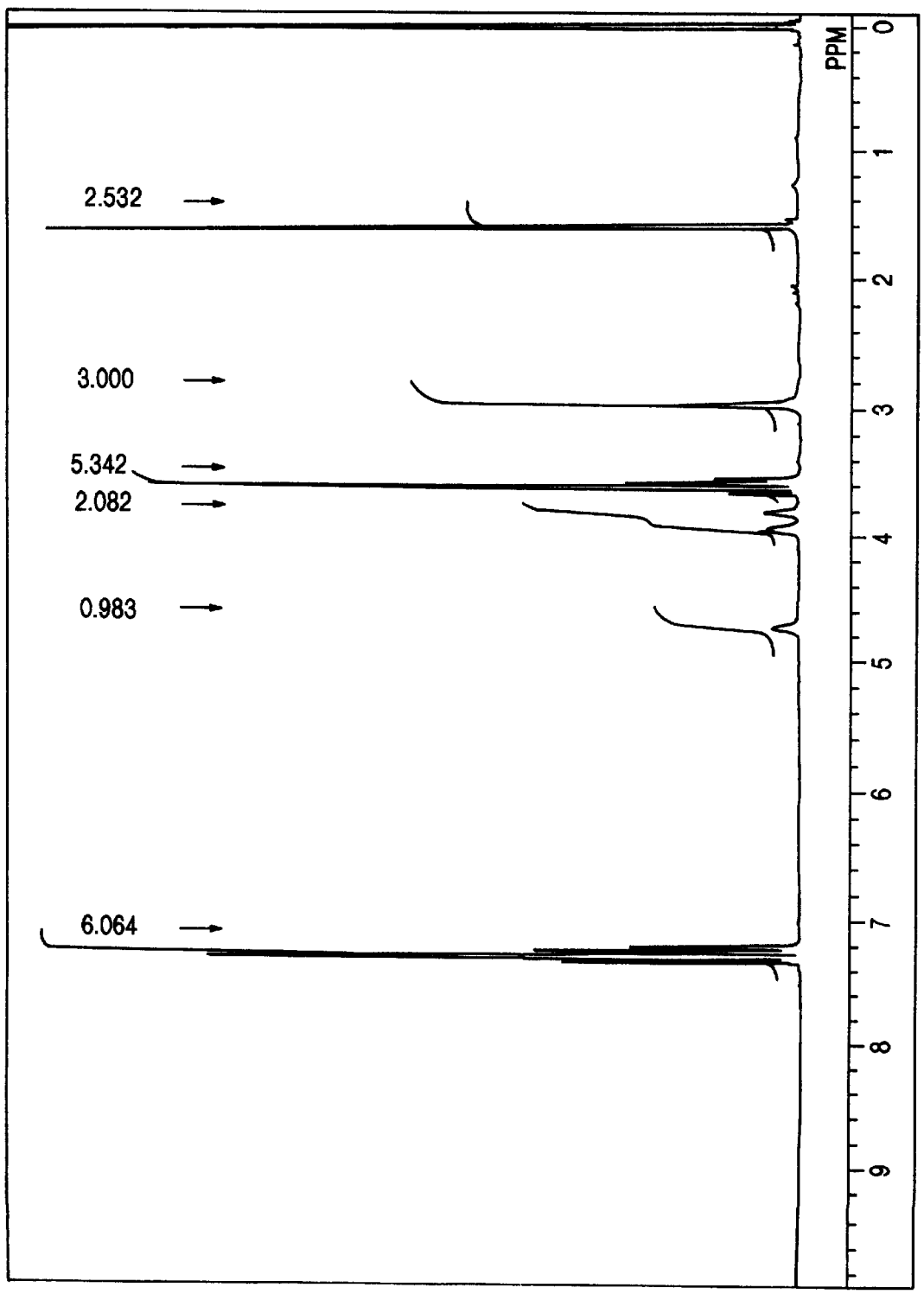
FIG. 3 shows an NMR sepctrum of the product obtained in Example 8, namely methyl [1(S)-benzyl-2(S)-hydroxy-3-chloropropyl]carbamate.
Figure 4:
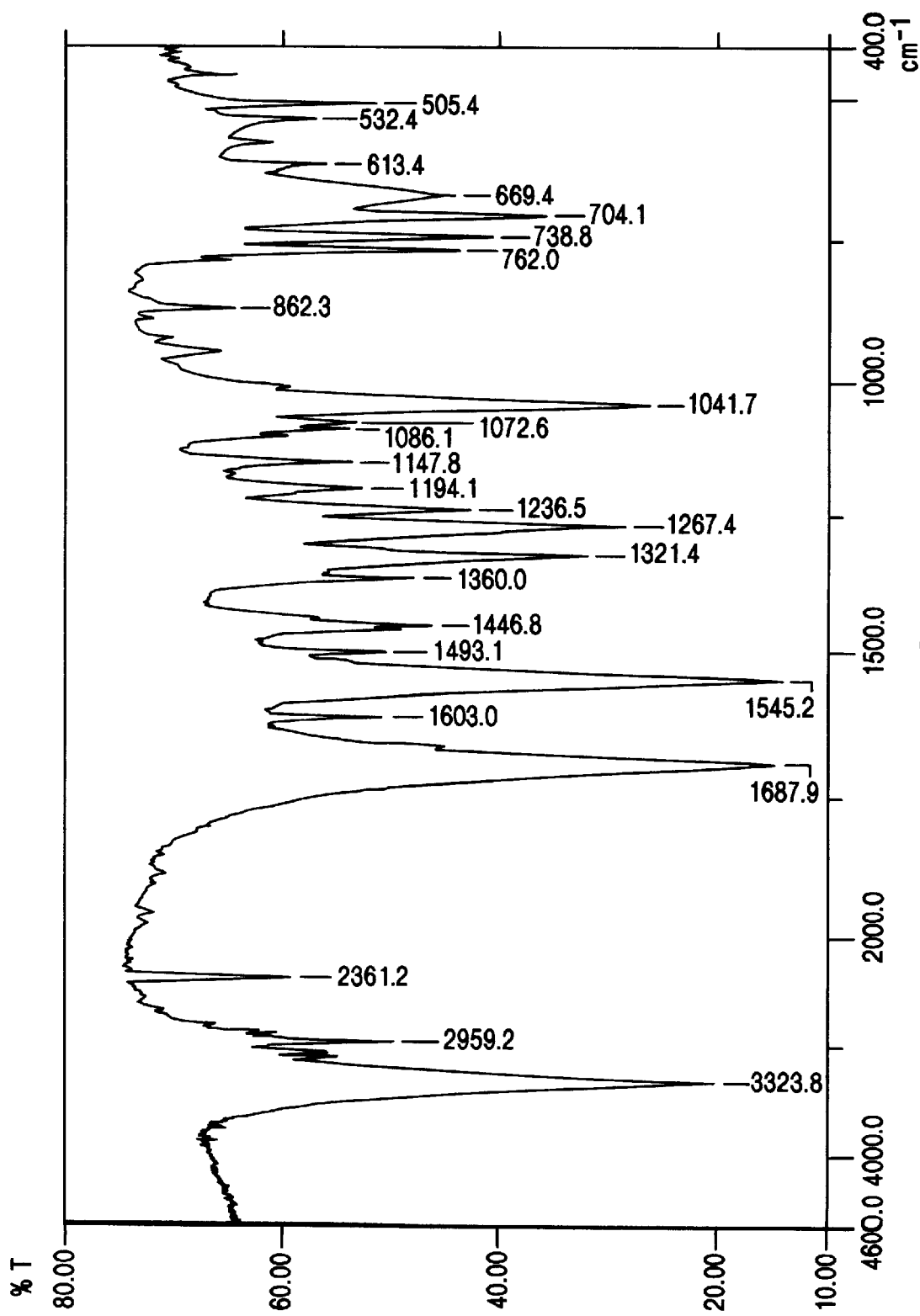
FIG. 4 shows an IR spectrum of the product obtained in Example 8, namely methyl [1(S)-benzyl-2(S)-hydroxy-3-chloropropyl]carbamate.

An NMR spectrum of the thus-obtained product methyl [1(S)-benzyl-2(S)-hydroxy-3-chloropropyl]carbamate is shown in FIG. 3 and an IR spectrum of the same in FIG. 4.

EXAMPLE 9

Production of benzyl [1(R)-phenylthiomethyl-2(S)-hydroxy-3-chloropropyl]carbamate (III)

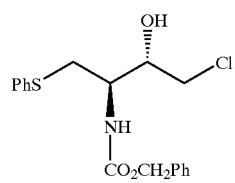

(III)

Figure 5:
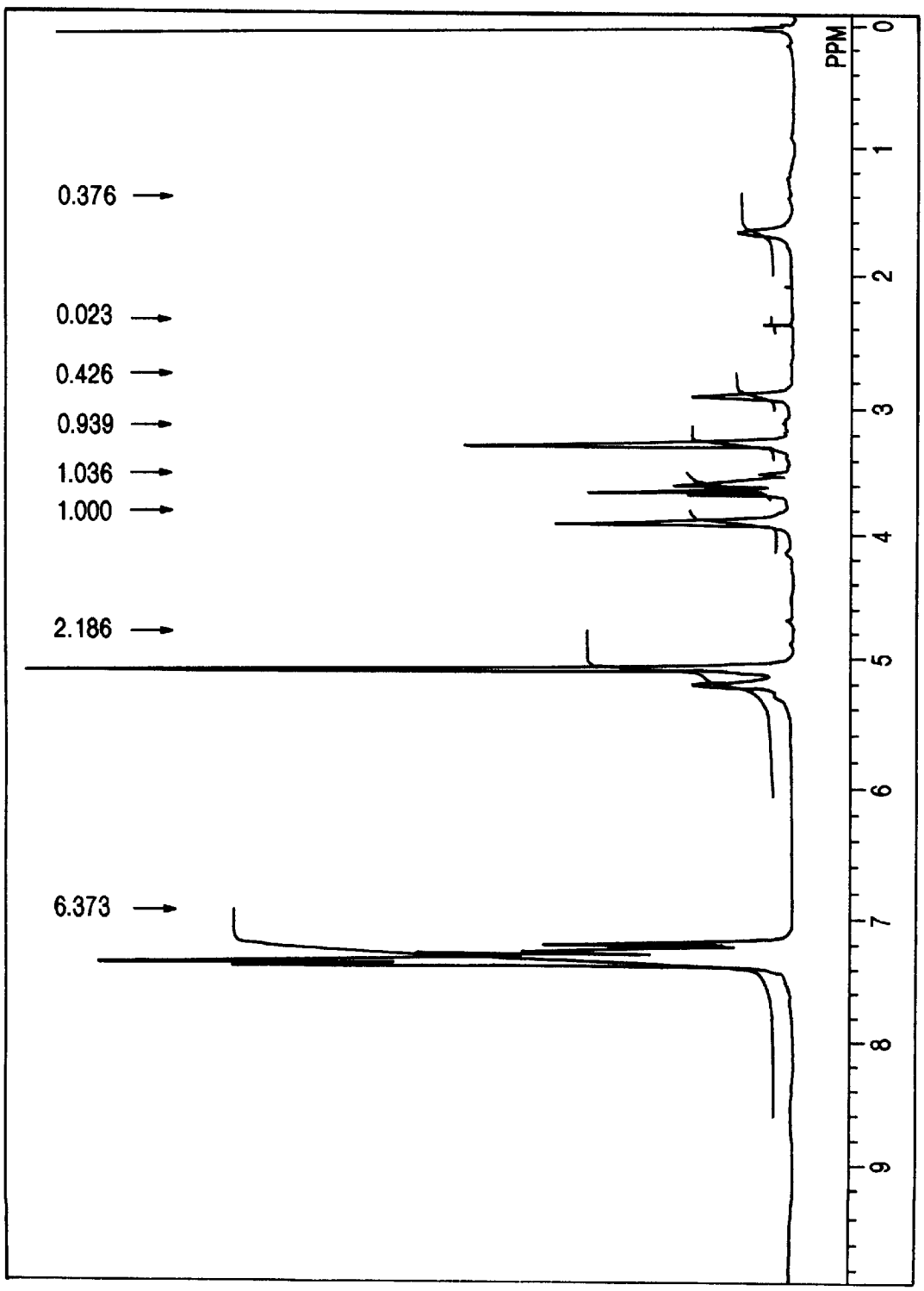
FIG. 5 shows an NMR sepctrum of the product obtained in Example 9, namely benzyl [1(R)-phenylthiomethyl-2(S)-hydroxy-3-chloropropyl]carbamate.
Figure 6:
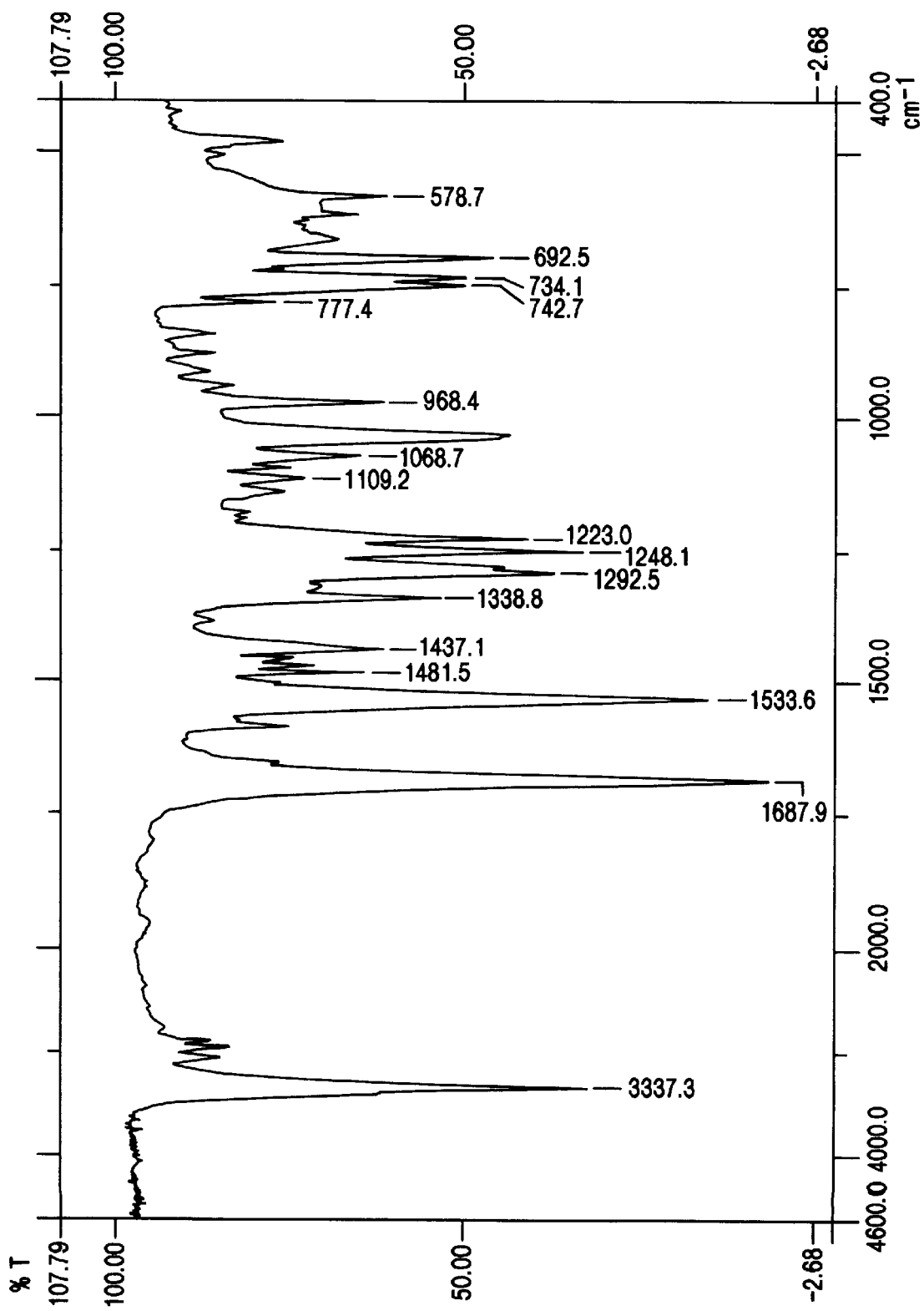
FIG. 6 shows an IR spectrum of the product obtained in Example 9, namely benzyl [1(R)-phenylthiomethyl-2(S)-hydroxy-3-chloropropyl]carbamate.

2-Propanol (26.44 g, 440 mmol) was added to 216 ml (220 mmol) of a toluene solution of DIBAH (1.02 M) at room temperature and the mixture was stirred at room temperature for 1 hour. Thereto was added 39.6 g (108.9 mmol) of t-benzyl [1(R)-phenylthiomethyl-2-oxo-3-chloropropyl]carbamate, and the resultant mixture was stirred at room temperature for 3 hours, followed by hydrolysis with 500 ml of 1 N hydrochloric acid with ice cooling. After extraction with 300 ml of ethyl acetate, the extract was washed in sequence with 500 ml of 2% aqueous sodium hydrogencarbonate and 200 ml of 2% aqueous sodium chloride, dried over with anhydrous magnesium sulfate and concentrated to give 75.6 g of a pale-yellow solid. The solid obtained was crystallized out from toluene/hexane to give 32.9 g of benzyl [1(R)-phenylthiomethyl-2(S)-hydroxy-3-chloropropyl]carbamate (yield 82.7). Analysis of the mother liquor by HPLC revealed the presence of 2.03 g of benzyl [1(R)-phenylthiomethyl-2(S)-hydroxy-3-chloropropyl]carbamate (yield 5.1%) and 1.753 g of benzyl [1(R)-phenylthiomethyl-2(R)-hydroxy-3-chloropropyl] carbamate (yield 4.4%). Selectivity with respect to the total of the reaction products: (1R,2S) form/(1R,2R) form=95.2/4.8. An NMR spectrum of the thus-obtained product benzyl [1(R)-phenylthiomethyl-2(S)-hydroxy-3-chloropropyl] carbamate is shown in FIG. 5 and an IR spectrum of the same in FIG. 6.

EXAMPLE 10

Production of benzyl alcohol

2-Propanol (1.53 ml, 20 mmol) was added to 9.8 ml (10 mmol) of a toluene solution of DIBAH (1.02 M) at room temperature and the mixture was stirred at room temperature for 1 hour. Thereto was added 0.531 g of benzaldehyde, and the resultant mixture was stirred at room temperature for 2 hours and then hydrolyzed with 1 N hydrochloric acid with ice cooling. Extraction with ethyl acetate and concentration gave 615 mg of benzyl alcohol as an oil. HPLC analysis of the oil obtained revealed a conversion of 99.9% and a yield of 78.0%.

EXAMPLE 11

Production of 1-phenyl-2-chloroethanol

The procedure of Example 10 was followed using 0.773 g (5 mmol) of phenacyl chloride in lieu of benzaldehyde, to give 809 mg of 1-phenyl-2-chloroethanol as an oil. Conversion rate: 97.5%; yield 80.4%.

EXAMPLE 12

Production of α-phenethyl alcohol

2-Propanol (1.53 ml, 20 mmol) was added to 9.9 ml (10 mmol) of a toluene solution of DIBAH (1.02 M) at room temperature and the mixture was stirred at room temperature for 1 hour. Thereto was added 0.601 g of acetophenone, and the resultant mixture was stirred at room temperature for 6 hours, followed by hydrolysis with 1 N hydrochloric acid with ice cooling. Extraction with ethyl acetate and concentration gave 1.001 g of α-phenethyl alcohol as an oil. Conversion 55%, yield 47.7%.

EXAMPLE 13

Production of α-phenethyl alcohol

Benzhydrol (3.68 g, 20 mmol) was added to 9.9 ml (10 mmol) of a toluene solution of DIBAH (1.02 M) at room temperature and the mixture was stirred at room temperature for 1 hour. Thereto was added 0.601 g (5 mmol) of acetophenone, and the resultant mixture was stirred at room temperature for 2 hours, followed by hydrolysis with 1 N hydrochloric acid with ice cooling. Extraction with ethyl acetate and concentration gave an oil, which was subjected to quantitative analysis by HPLC. Thus was confirmed the formation of α-phenethyl alcohol in 42.3% yield (conversion 53.3%).

EXAMPLE 14

Production of Methyl 2(S)-hydroxy-3(S)-(t-butoxycarbonylamino)-4-phenylbutyrate (IV)

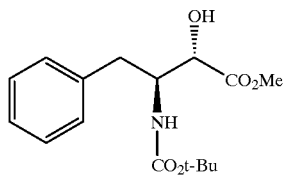

(IV)

Benzhydrol (0.737 g, 4 mmol) was added to 2 ml (2.04 mmol) of a toluene solution of DIBAH (1.02 M) at room temperature and the mixture was stirred at room temperature for 1 hour. Thereto was added 0.307 g (1 mmol) of methyl 3(S)-(t-butoxycarbonylamino)-2-oxo-4-phenylbutyrate, and the resultant mixture was stirred at room temperature for 2 hours, followed by hydrolysis with 1 N hydrochloric acid with ice cooling. Extraction with ethyl acetate, concentration of the extract and purification of the thus-obtained oil by preparative TLC gave 217 mg of a mixture of methyl 2(S)-hydroxy-3(S)-(t-butoxycarbonylamino)-4-phenylbutyrate and methyl 2(R)-hydroxy-3-(S)-(t-butoxycarbonylamino)-4-phenylbutyrate. Upon HPLC analysis, the diastereoselectivity was found to be (2S,3S)/(2R,3S)=94/6.

Yields: methyl 2(S)-hydroxy-3(S)-(t-butoxycarbonylamino)-4-phenylbutyrate 65.9%; methyl 2(R)-hydroxy-3-(S)-(t-butoxycarbonylamino)-4-phenylbutyrate 4.2%.

Figure 7:
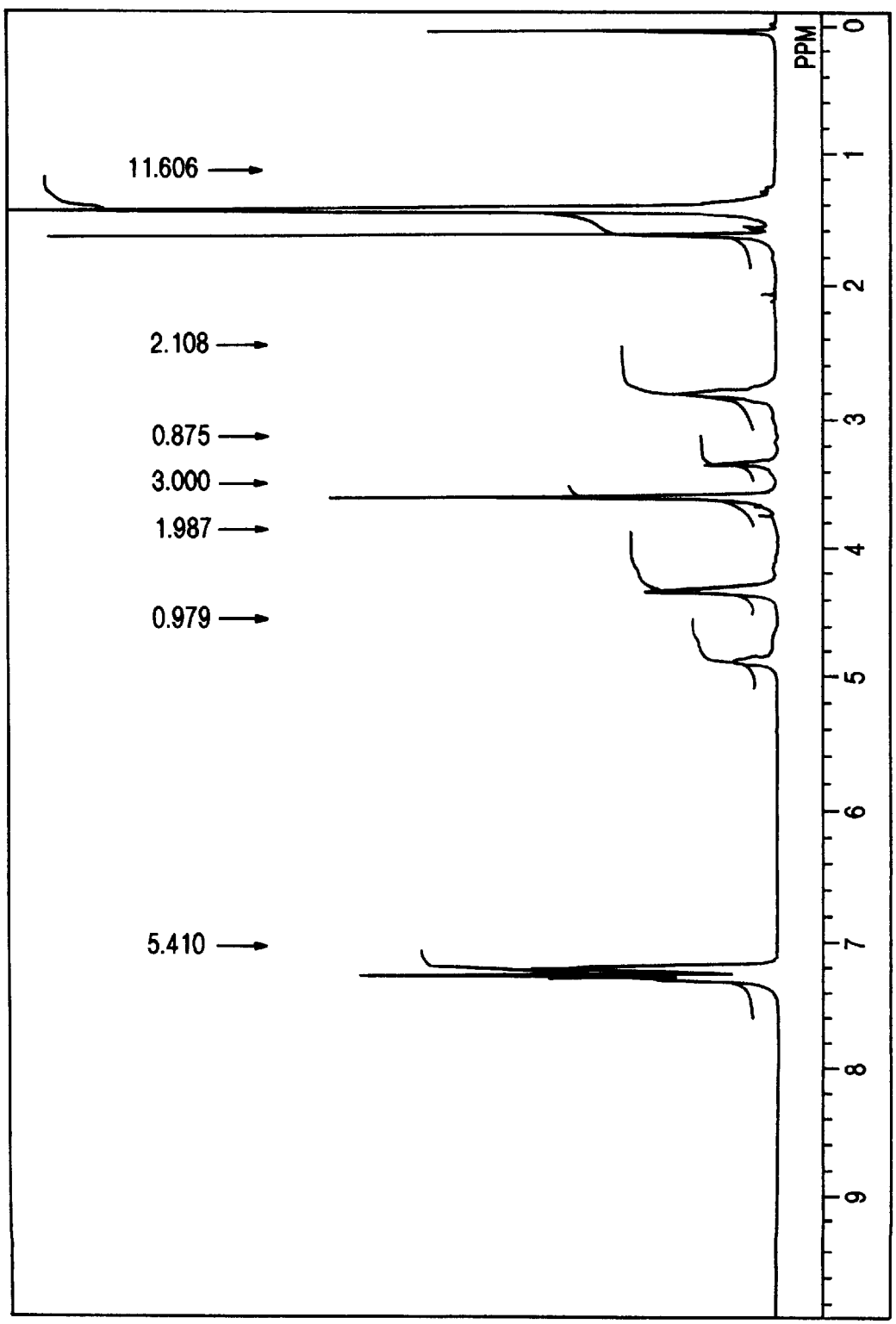
FIG. 7 shows an NMR sepctrum of the product obtained in Example 14, namely methyl 2(R,S)-hydroxy-3(S)-(t-butoxycarbonylamino)-4-phenylbutyrate.
Figure 8:
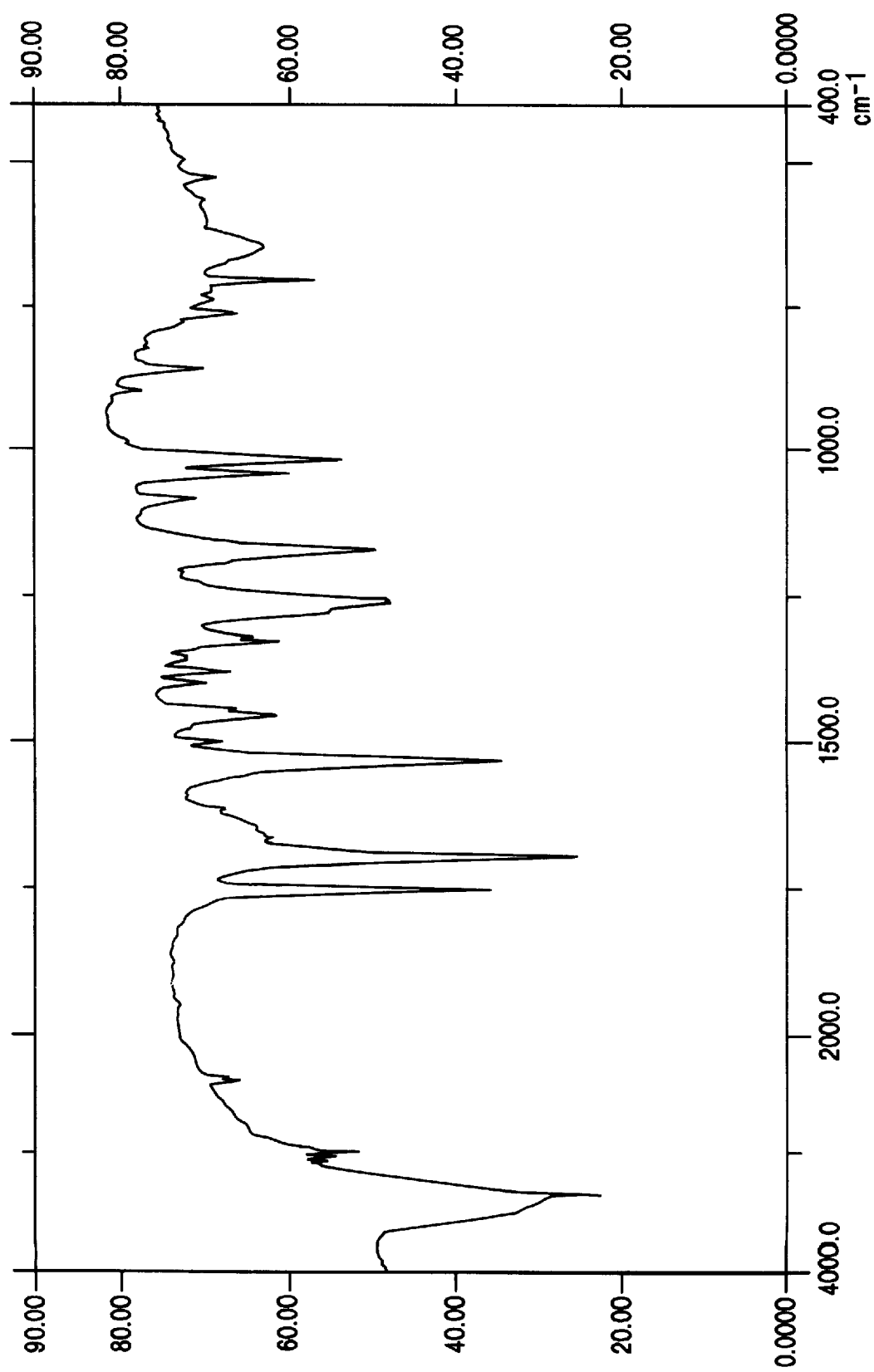
FIG. 8 shows an IR spectrum of the product obtained in Example 14, namely methyl 2(R,S)-hydroxy-3(S)-(t-butoxycarbonylamino)-4-phenylbutyrate.

An NMR spectrum of the thus-obtained product methyl 2(R,S)-hydroxy-3(S)-(t-butoxycarbonylamino)-4-phenylbutyrate is shown in FIG. 7 and an IR spectrum of the same in FIG. 8.

EXAMPLE 15

Production of Ethyl [1(S)-benzyl-3,3-dichloro-2(S)-hydroxypropyl]carbamate (V)

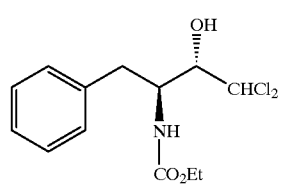

(V)

2-Propanol (920 mg, 1.5 mmol) was added to 0.73 ml (0.74 mmol) of a toluene solution of DIBAH (1.01 M) at room temperature and the mixture was stirred at room temperature for 1 hour. Thereto was added 100 mg (0.33 mmol) of ethyl [1(S)-benzyl-3,3-dichloro-2-oxopropyl] carbamate, and the resultant mixture was stirred at room temperature for 3.5 hours, then at 40° C. for 2 hours and, further, at room temperature for 15 hours, followed by hydrolysis with 1 N hydrochloric acid with ice cooling. Extraction with ethyl acetate and concentration of the extract gave an oil, which was purified by preparative TLC to give 66.7 mg (0.22 mmol) of a mixture of ethyl [1(S)-benzyl-3,3-dichloro-2(S)-hydroxypropyl]carbamate and ethyl [1(S)-benzyl-3,3-dichloro-2(R)-hydroxypropyl]carbamate. The diastereoselectivity as determined by HPLC was (1S,2S)/(1S,2R)=95/5.

Yields: ethyl [1(S)-benzyl-2(S)-hydroxy-3,3-dichloropropyl]carbamate 62.7%; ethyl [1(S)-benzyl-2(R)-hydroxy-3,3-dichloropropyl]carbamate 33%.

Figure 9:
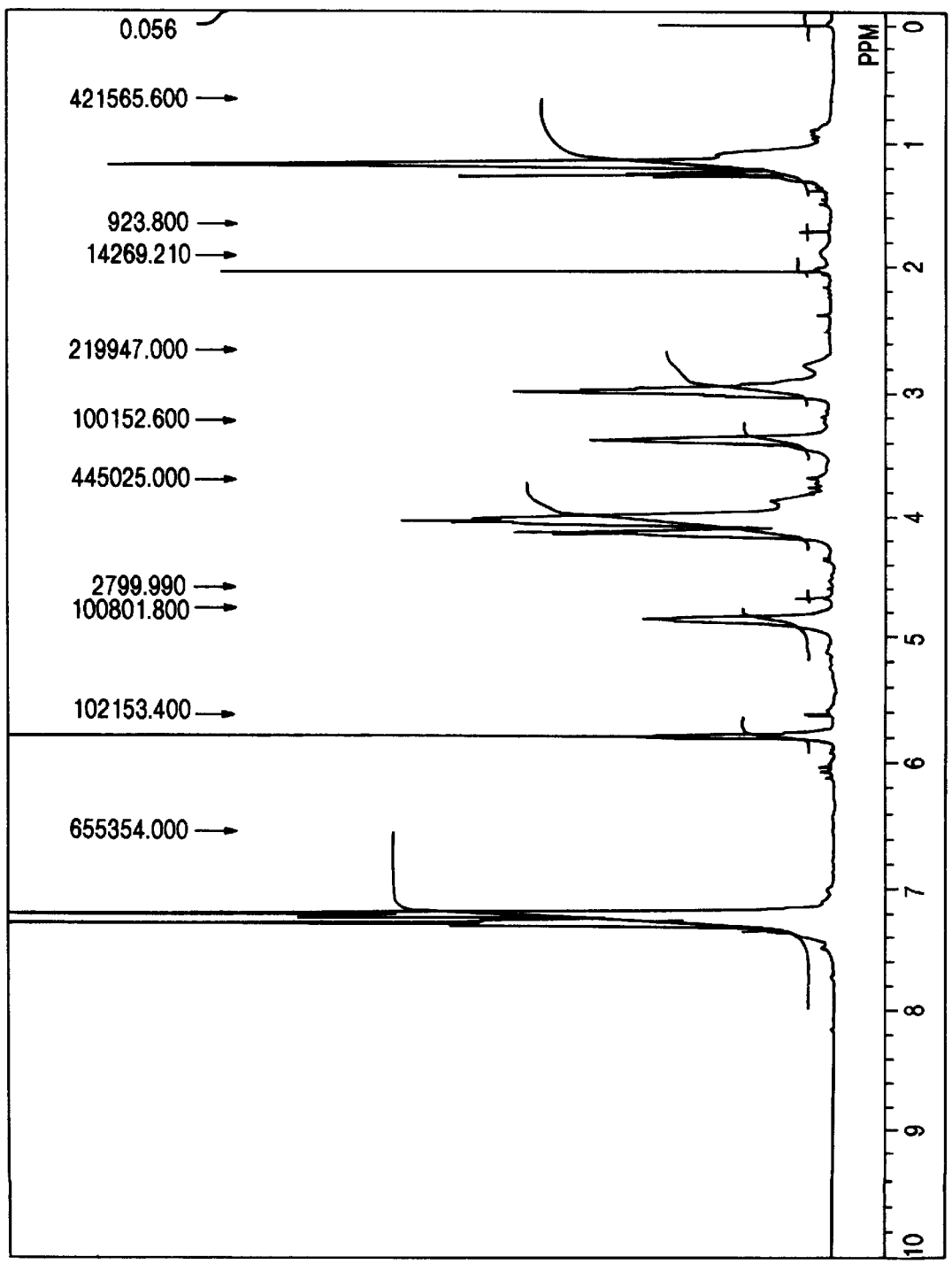
FIG. 9 shows an NMR sepctrum of the product obtained in Example 15, namely ethyl [1(S)-benzyl-2(R,S)-hydroxy-3,3-dichloropropyl]carbamate.
Figure 10:
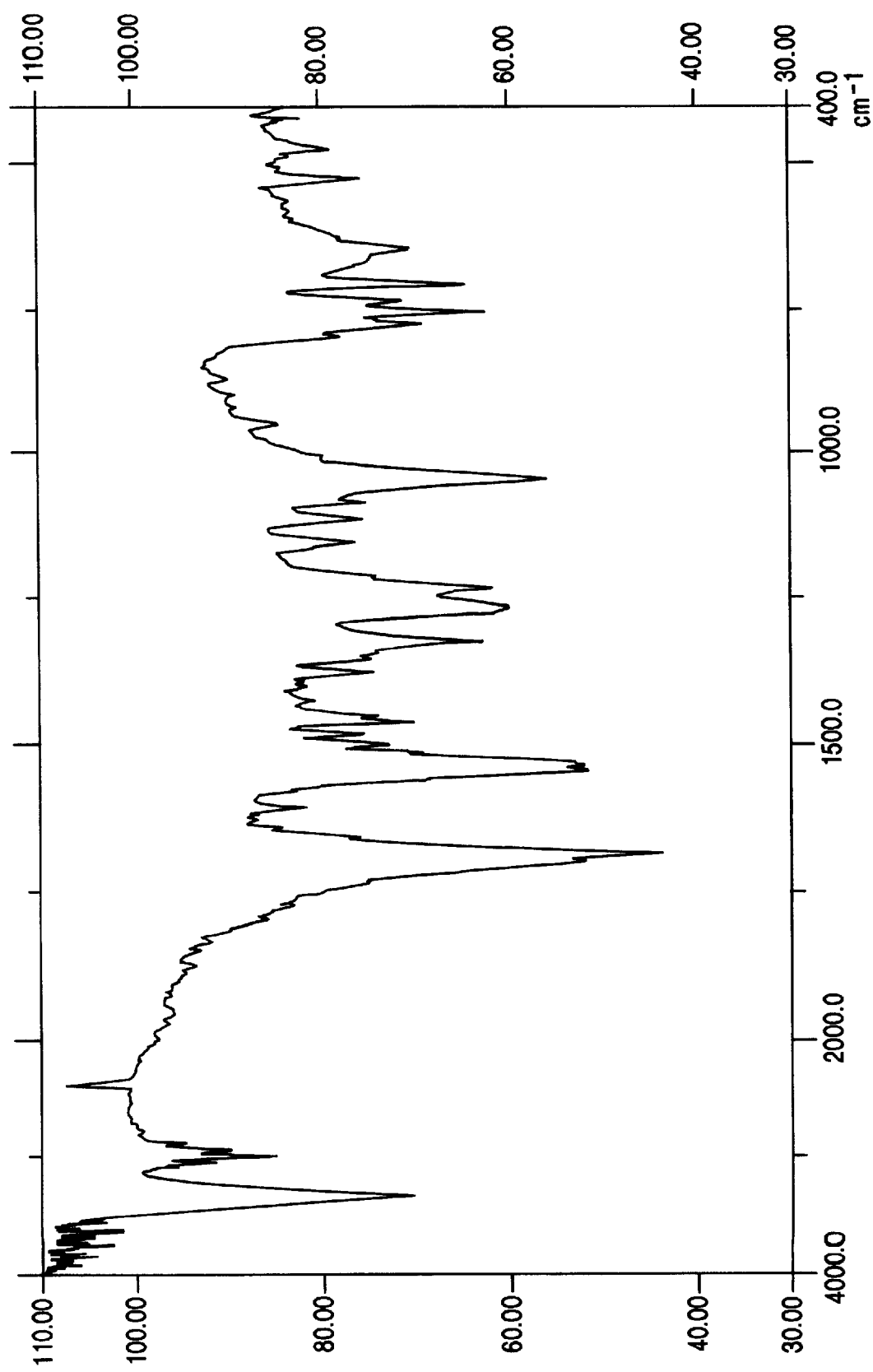
FIG. 10 shows an IR spectrum of the product obtained in Example 15, namely ethyl [1(S)-benzyl-2(R,S)-hydroxy-3,3-dichloropropyl]carbamate.

An NMR spectrum of the thus-obtained product ethyl [1(S)-benzyl-3,3-dichloro-2(R,S)-hydroxypropyl]carbamate is shown in FIG. 9 and an IR spectrum of the same in FIG. 10.

Reference Example 1

Production of t-butyl [1(S)-benzyl-2(S),3-epoxypropyl]carbamate

A 0.976-g portion of the product obtained in Example 1, namely t-butyl [1(S)-benzyl-2(S)-hydroxy-3-chloropropyl] carbamate, was suspended in 8 ml of acetone, then 2 ml of 10% sodium hydroxide was added, and the mixture was stirred at room temperature for 1 hour. The aqueous layer was separated and the organic layer was concentrated to dryness to give t-butyl [1(S)-benzyl-2(S),3-epoxypropyl] carbamate. After purification by preparative TLC, the optical purity (99.8% ee) was confirmed using a chiral column.

Reference Example 2

Production of α-phenethyl Alcohol

Acetophenone (0.601 g) was dissolved in 15 ml of 2-propanol, 2.04 g of aluminum triisopropoxide was added, and the mixture was stirred at 25° C. for 4 hours. After hydrolysis with 1 N hydrochloric acid, the mixture was extracted with ethyl acetate. Concentration gave 0.564 g of an oil, which was analyzed by HPLC (conversion 0.6%, yield 0.4%).

Reference Example 3

Reduction of methyl 3(S)-(t-butoxycarbonylamino)-2-oxo-4-phenylbutyrate with Al(O-iPr)$_3$ Methyl 3(S)-(t-butoxycarbonylamino)-2-oxo-4-phenylbutyrate (307 mg) was dissolved in 6 ml of 2-propanol, 204 mg (2 mmol) of Al(O-iPr)$_3$ was added, and the mixture was stirred at room temperature for 1 hour and then at 50° C. for further 15 hours. However, the formation of the reduction product methyl 2(R,S)-hydroxy-3(S)-(t-butoxycarbonylamino)-4-phenylbutyrate was scarcely observed.

Industrial Applicability

Being constituted as mentioned above, the present invention makes it possible to reduce carbonyl compounds to the corresponding hydroxy compounds in a simple and easy manner at a lower temperature with high stereoselectivity. Thus, for example, the invention makes it possible to produce aminohalohydrin derivatives, which are intermediates in the production of useful medicinal compounds, from aminohaloketone derivatives derived from phenylalanine and the like, under mild conditions with very high stereoselectivity.

What is claimed is:

1. A process for reducing carbonyl compounds which comprises reacting a carbonyl compound of the general formula (1)

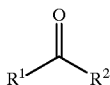
(1)

wherein R$^1$ and R$^2$ each independently represents a substituted or unsubstituted alkyl group containing 1 to 30 carbon atoms, a substituted or unsubstituted aralkyl group containing 7 to 30 carbon atoms, a substituted or unsubstituted aryl group containing 6 to 30 carbon atoms, a cyano group, a hydrogen atom, a group of the general formula (2)

$$CH_nX_{3-n} \quad (2)$$

in which X represents a halogen atom and n represents an integer of 0 to 2, or a group of the general formula (3)

(3)

in which Y represents an alkoxyl group, an aralkyloxyl group, an amino group, an alkylamino group or an alkylthio group, provided that one of R$^1$ and R$^2$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms, with an organoaluminum compound of the general formula (4)

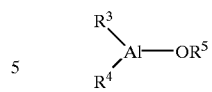
(4)

wherein R$^3$ and R$^4$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms and R$^5$ represents a substituted or unsubstituted primary alkyl group containing 1 to 20 carbon atoms, a substituted or unsubstituted secondary alkyl group containing 1 to 20 carbon atoms, a substituted or unsubstituted primary aralkyl group containing 7 to 30 carbon atoms or a substituted or unsubstituted secondary aralkyl group containing 7 to 30 carbon atoms, to provide the corresponding alcohol compound of the general formula (5)

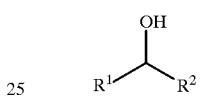
(5)

wherein R$^1$ and R$^2$ are as defined above.

2. The process for reducing carbonyl compounds according to claim 1, wherein the organoaluminum compound of general formula (4) is diisobutylaluminum isopropoxide or diisobutylaluminum diphenylmethoxide.

3. A process for reducing carbonyl compounds which comprises reacting a carbonyl compound of the general formula (1)

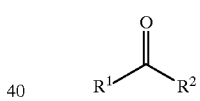
(1)

wherein R$^1$ and R$^2$ each independently represents a substituted or unsubstituted alkyl group containing 1 to 30 carbon atoms, a substituted or unsubstituted aralkyl group containing 7 to 30 carbon atoms, a substituted or unsubstituted aryl group containing 6 to 30 carbon atoms, a cyano group, a hydrogen atom, a group of the general formula (2)

$$CH_nX_{3-n} \quad (2)$$

in which X represents a halogen atom and n represents an integer of 0 to 2, or a group of the general formula (3)

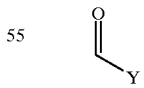
(3)

in which Y represents an alkoxyl group, an aralkyloxyl group, an amino group, an alkylamino group or an alkylthio group, provided that one of R$^1$ and R$^2$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms, with a compound prepared in advance from an organoaluminum compound of the general formula (10)

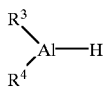
(10)

wherein $R^3$ and $R^4$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms, and an alcohol compound of the general formula (11)

(11)

wherein $R^5$ represents a substituted or unsubstituted primary alkyl group containing 1 to 20 carbon atoms, a substituted or unsubstituted secondary alkyl group containing 1 to 20 carbon atoms, a substituted or unsubstituted primary aralkyl group containing 7 to 30 carbon atoms or a substituted or unsubstituted secondary aralkyl group containing 7 to 30 carbon atoms or a cycloalkyl group, to provide the corresponding alcohol compound of the general formula (5)

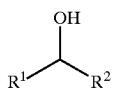
(5)

wherein $R^1$ and $R^2$ are as defined above.

4. The process for reducing carbonyl compounds according to claim 3, wherein the organoaluminum compound of general formula (10) is diisobutylaluminum hydride.

5. The process for reducing carbonyl compounds according to claim 3, wherein the alcohol compound of general formula (11) is an alcohol compound of the general formula (12)

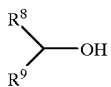
(12)

in which $R^8$ and $R^9$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms or $R^8$ in combination with $R^9$ represent a cycloalkyl group.

6. The process for reducing carbonyl compounds according to claim 5, wherein the alcohol compound of general formula (12) is isopropanol.

7. The process for reducing carbonyl compounds according to claim 5, wherein the alcohol compound of general formula (12) is benzhydrol.

8. The process for reducing carbonyl compounds according to claim 1, wherein the reduction reaction is carried out at a temperature of $-10°$ C. to $30°$ C.

9. The process for reducing carbonyl compounds according to claim 1, wherein, in the carbonyl compound of general formula (1), $R^1$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms and $R^2$ is a group of the general formula (2)

(2)

in which X represents a halogen atom and n represents an integer of 0 to 2, or a group of the general formula (3)

(3)

in which Y represents an alkoxyl group, an aralkyloxyl group, an amino group, an alkylamino group or an alkylthio group.

10. The process for reducing carbonyl compounds according to claim 3 wherein the reduction reaction is carried out at a temperature of $-10°$ C. to $30°$ C.

11. The process for reducing carbonyl compounds according to claim 3 wherein, in the carbonyl compound of general formula (1), $R^1$ is a substituted or unsubstituted alkyl group containing 1 to 30 carbon atoms, a substituted or unsubstituted aralkyl group containing 7 to 30 carbon atoms or a substituted or unsubstituted aryl group containing 6 to 30 carbon atoms and $R^2$ is a group of the general formula (2)

(2)

in which X represents a halogen atom and n represents an integer of 0 to 2, or a group of the general formula (3)

(3)

in which Y represents an alkoxyl group, an aralkyloxyl group, an amino group, an alkylamino group or an alkylthio group.

12. The process for reducing carbonyl compounds according to claim 1 wherein said carbonyl compound of the formula (1) is an α-aminoketone derivative of the general formula (6)

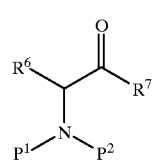
(6)

wherein $R^6$ represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms or a hydrogen atom, $R^7$ represents a group of the general formula (2)

(2)

in which X represents a halogen atom and n represents an integer of 0 to 2, or a group of the general formula (3)

(3)

in which Y represents an alkoxyl group, an aralkyloxyl group, an amino group, an alkylamino group or an alkylthio group, and $P^1$ and $P^2$ each independently represents a hydrogen atom or an amino-protecting group or $P^1$ in combination with $P^2$ represent a phthaloyl group, with the exception of the case in which $P^1$ and $P^2$ are the same and each is a hydrogen atom, and said corresponding compound of the formula (5) is the general formula (8)

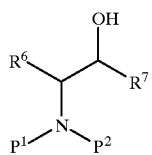
(8)

wherein $R^6$, $R^7$, $P^1$ and $P^2$ are as defined above.

13. The process for reducing carbonyl compound according to claim 12, wherein the organoaluminum compound of general formula (4) is diisobutylaluminum isopropoxide or diisobutylaluminum diphenylmethoxide.

14. A process for reducing carbonyl compounds according to claim 3, wherein said carbonyl compound of formula (1) is an α-aminoketone compound of the formula (6)

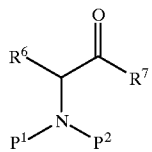
(6)

wherein $R^6$ represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms, or a hydrogen atom, $R^7$ represents a group of the general formula (2)

(2)

in which X represents a halogen atom and n represents an integer of 0 to 2, or a group of the general formula (3)

(3)

in which Y represents an alkoxyl group, an aralkyloxyl group, an amino group, an alkylamino group or an alkylthio group, and $P^1$ and $P^2$ are the same and each is a hydrogen atom, said corresponding compound of the formula (5) is the general formula (8)

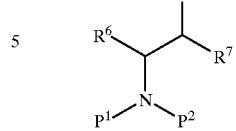
(8)

wherein $R^6$, $R^7$, $P^1$ and $P^2$ are as defined above.

15. The process for reducing carbonyl compounds according to claim 14, wherein the organoaluminum compound of general formula (10) is diisobutylaluminum hydride.

16. The process for reducing carbonyl compounds according to claim 14, wherein the alcohol compound of the general formula (11) is an alcohol compound of the general formula (12)

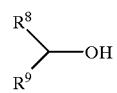
(12)

in which $R^8$ and $R^9$ each independently represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms or $R^8$ in combination with $R^9$ represent a cycloalkyl group.

17. The process for reducing carbonyl compounds according to claim 16, wherein the alcohol compound of general formula (12) is isopropanol.

18. The process for reducing carbonyl compounds according to claim 16, wherein the alcohol compound of general formula (12) is benzhydrol.

19. The process for reducing carbonyl compounds according to claim 12, wherein the reduction reaction is carried out at a temperature of −10° C. to 30° C.

20. The process for reducing carbonyl compounds according to claim 12, wherein one of $P^1$ and $P^2$ in the α-aminoketone derivative of general formula (6) is a hydrogen atom and the other is an amino-protecting alkoxycarbonyl or aralkyloxycarbonyl group.

21. The process for reducing carbonyl compounds according to claim 12, wherein the α-aminoalcohol derivative of general formula (11) is obtained stereoselectively in the erythro form.

22. The process for reducing carbonyl compounds according to claim 12, wherein the α-aminoketone derivative of general formula (6) is an α-aminohaloketone derivative of the general formula (7)

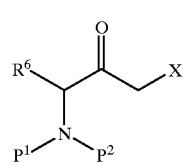
(7)

in which X represents a halogen atom, $R^6$ represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms or a hydrogen atom and $P^1$ and $P^2$ each independently represents a hydrogen atom or an amino-protecting group or $P^1$ in combination with $P^2$ represent a phthaloyl group, with the exception of the case in which $P^1$ and $P^2$ are the same and each is a hydrogen atom, and the α-aminoalcohol derivative of general formula (8) is the α-aminohalohydrin derivative of the general formula (9)

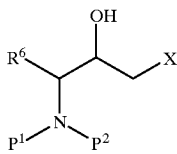

(9)

in which X, $R^6$, $P^1$ and $P^2$ are as defined above.

23. The process for reducing carbonyl compounds according to claim 22, wherein the α-aminohaloketone derivative of general formula (7) is optically active t-butyl (S)-(1-benzyl-3-chloro-2-oxopropyl)carbamate,
t-butyl (R)-(1-benzyl-3-chloro-2-oxopropyl)carbamate,
methyl (S)-(1-benzyl-3-chloro-2-oxopropyl)carbamate,
methyl (R)-(1-benzyl-3-chloro-2-oxopropyl)carbamate,
ethyl (S)-(1-benzyl-3-chloro-2-oxopropyl)carbamate,
ethyl (R)-(1-benzyl-3-chloro-2-oxopropyl)carbamate,
benzyl (R)-(1-benzyl-3-chloro-2-oxopropyl)carbamate,
benzyl (S)-(1-benzyl-3-chloro-2-oxopropyl)carbamate,
benzyl (R)-(1-phenylthiomethyl-3-chloro-2-oxopropyl) carbamate,
benzyl (S)-(1-phenylthiomethyl-3-chloro-2-oxopropyl) carbamate,
t-butyl (S)-(1-phenylthiomethyl-3-chloro-2-oxopropyl) carbamate,
t-butyl (R)-(1-phenylthiomethyl-3-chloro-2-oxopropyl) carbamate,
methyl (S)-(1-phenylthiomethyl-3-chloro-2-oxopropyl) carbamate,
methyl (R)-(1-phenylthiomethyl-3-chloro-2-oxopropyl) carbamate,
ethyl (S)-(1-phenylthiomethyl-3-chloro-2-oxopropyl) carbamate,
ethyl (R)-(1-phenylthiomethyl-3-chloro-2-oxopropyl) carbamate.

24. The process for reducing carbonyl compounds according to claim 22, wherein the α-aminohaloketone derivative of general formula (7) is t-butyl (S)-(1-benzyl-3-chloro-2-oxopropyl)carbamate or benzyl (S)-(1-phenylthiomethyl-3-chloro-2-oxopropyl)carbamate, the organoaluminum compound of general formula (4) is diisobutylaluminum hydride and the alcohol compound of general formula (5) is isopropanol or benzhydrol.

25. The process for reducing carbonyl compounds according to claim 22, wherein the α-aminohalohydrin derivative of general formula (9) is obtained stereoselectively in the erythro form.

26. The process for reducing carbonyl compounds according to claim 14, wherein the reduction reaction is carried out at a temperature of −10° C. to 30°.

27. The process for reducing carbonyl compounds according to claim 14, wherein one of $P^1$ and $P^2$ in the α-aminoketone derivative of general formula (6) is a hydrogen atom and the other is an amino-protecting alkoxycarbonyl or aralkyloxycarbonyl group.

28. The process for reducing carbonyl compounds according to claim 14, wherein the α-aminoalcohol derivative of general formula (11) is obtained stereoselectively in the erythro form.

29. The process for reducing carbonyl compounds according to claim 14, wherein the α-aminoketone derivative of general formula (6) is an α-aminohaloketone derivative of the general formula (7)

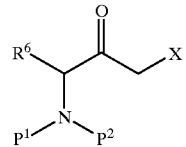

(7)

in which X represents a halogen atom, $R_6$ represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms or a hydrogen atom and $P^1$ and $P^2$ each independently represents a hydrogen atom or an amino-protecting group or $P^1$ in combination with $P^2$ represent a phthaloyl group, with the exception of the case in which $P^1$ and $P^2$ are the same and each is a hydrogen atom, and the α-aminoalcohol derivative of general formula (8) is the α-aminohalohydrin derivative of the general formula (9)

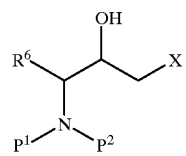

(9)

in which X, $R^5$, $P^1$ and $P^2$ are as define above.

30. The process for reducing carbonyl compounds according to claim 29, wherein the α-aminohaloketone derivative of general formula (7) is optically active t-butyl (S)-(1-benzyl-3-chloro-2-oxopropyl)carbamate,
t-butyl (R)-(1-benzyl-3-chloro-2-oxopropyl)carbamate,
methyl (S)-(1-benzyl-3-chloro-2-oxopropyl)carbamate,
methyl (R)-(1-benzyl-3-chloro-2-oxopropyl)carbamate,
ethyl (S)-(1-benzyl-3-chloro-2-oxopropyl)carbamate,
ethyl (R)-(1-benzyl-3-chloro-2-oxopropyl)carbamate,
benzyl (R)-(1-benzyl-3-chloro-2-oxopropyl)carbamate,
benzyl (S)-(1-benzyl-3-chloro-2-oxopropyl)carbamate,
benzyl (R)-(1-phenylthiomethyl-3-chloro-2-oxopropyl) carbamate,
benzyl (S)-(1-phenylthiomethyl-3-chloro-2-oxopropyl) carbamate,
t-butyl (S)-(1-phenylthiomethyl-3-chloro-2-oxopropyl) carbamate,
t-butyl (R)-(1-phenylthiomethyl-3-chloro-2-oxopropyl) carbamate,
methyl (S)-(1-phenylthiomethyl-3-chloro-2-oxopropyl) carbamate,
methyl (R)-(1-phenylthiomethyl-3-chloro-2-oxopropyl) carbamate,
ethyl (S)-(1-phenylthiomethyl-3-chloro-2-oxopropyl) carbamate,
ethyl (R)-(1-phenylthiomethyl-3-chloro-2-oxopropyl) carbamate.

31. The process for reducing carbonyl compounds according to claim 29, wherein the α-aminohaloketone derivative of general formula (7) is t-butyl (S)-(1-benzyl-3-chloro-2-oxopropyl)carbamate or benzyl (S)-(1-phenylthiomethyl-3-chloro-2-oxopropyl)carbamate, the organoaluminum compound of general formula (4) is diisobutylaluminum hydride and the alcohol compound of general formula (5) is isopropanol or benzhydrol.

32. The process for reducing carbonyl compounds according to claim 29, wherein the α-aminohalohydrin derivative of general formula (9) is obtained stereoselectively in the erythro form.

* * * * *